US012797833B2

(12) United States Patent
Xiang et al.

(10) Patent No.: US 12,797,833 B2
(45) Date of Patent: Nov. 17, 2026

(54) HYDROGENATION CATALYST, PREPARATION METHOD FOR SAME, APPLICATIONS THEREOF, AND HYDROGENATION REACTION METHOD

(71) Applicant: Hunan Changlian New Material Technology Co., Ltd., Yueyang City (CN)

(72) Inventors: Minglin Xiang, Yueyang City (CN); Bo Ao, Yueyang City (CN); Yongjun Wang, Yueyang City (CN); Dongjing Zhou, Yueyang City (CN); Zhenxing Jian, Yueyang City (CN); Xichun She, Yueyang City (CN)

(73) Assignee: HUNAN CHANGLIAN NEW MATERIAL TECHNOLOGY CO., LTD., Yueyang City (CN)

( * ) Notice: Subject to any disclaimer, the term of this patent is extended or adjusted under 35 U.S.C. 154(b) by 648 days.

(21) Appl. No.: 18/258,121

(22) PCT Filed: Nov. 25, 2021

(86) PCT No.: PCT/CN2021/133098
§ 371 (c)(1),
(2) Date: Jun. 16, 2023

(87) PCT Pub. No.: WO2022/127551
PCT Pub. Date: Jun. 23, 2022

(65) Prior Publication Data
US 2024/0123432 A1 Apr. 18, 2024

(30) Foreign Application Priority Data
Dec. 18, 2020 (CN) ........................ 202011513316.2

(51) Int. Cl.
*B01J 23/883* (2006.01)
*B01J 21/04* (2006.01)
(Continued)

(52) U.S. Cl.
CPC ............. *B01J 23/883* (2013.01); *B01J 21/04* (2013.01); *B01J 21/066* (2013.01); *B01J 35/394* (2024.01);
(Continued)

(58) Field of Classification Search
CPC .......... C07C 29/17; C07C 29/19; C07C 29/20
See application file for complete search history.

(56) References Cited

U.S. PATENT DOCUMENTS 2,118,954 A 5/1938 Thomas
4,192,960 A 3/1980 Hillion et al.

FOREIGN PATENT DOCUMENTS

CN 1362487 A 8/2002
CN 1375484 A 10/2002
(Continued)

OTHER PUBLICATIONS

Machine translation of CN102093161A, Jun. 15, 2011, pp. 1-25 (Year: 2011).*
(Continued)

*Primary Examiner* — Medhanit W Bahta
(74) *Attorney, Agent, or Firm* — CANTOR COLBURN LLP

(57) ABSTRACT

Disclosed are a hydrogenation catalyst, a preparation method for same, and applications thereof. Also disclosed is a hydrogenation reaction method employing the hydrogenation catalyst. The hydrogenation catalyst of the present invention comprises a binding agent and an active component. The active component comprises nickel and a group VIB metal element. The binding agent comprises zirconium
(Continued)

oxide and aluminum oxide. The catalyst of the present invention has nickel serving as the main active ingredient and is inexpensive. Moreover, the catalyst of the present invention exhibits an increased catalytic activity in a hydrogenation reaction of phenolic compounds and specifically provides an increased low-temperature reaction activity. The catalyst of the present invention is applicable in a continuous production process, thus implementing the continuous production of a hydrogenated bisphenol A product and providing the product with high and stable quality.

18 Claims, 1 Drawing Sheet

(51) Int. Cl.

| | |
|---|---|
| ***B01J 21/06*** | (2006.01) |
| ***B01J 35/30*** | (2024.01) |
| ***B01J 37/00*** | (2006.01) |
| ***B01J 37/02*** | (2006.01) |
| ***B01J 37/03*** | (2006.01) |
| ***B01J 37/04*** | (2006.01) |
| ***B01J 37/08*** | (2006.01) |
| ***B01J 37/18*** | (2006.01) |
| ***C07C 29/20*** | (2006.01) |
| ***C07C 35/21*** | (2006.01) |

(52) U.S. Cl.
CPC ....... *B01J 37/0009* (2013.01); *B01J 37/0236* (2013.01); *B01J 37/031* (2013.01); *B01J 37/04* (2013.01); *B01J 37/08* (2013.01); *B01J 37/18* (2013.01); *C07C 29/20* (2013.01); *C07C 35/21* (2013.01); *C07C 2601/14* (2017.05)

(56) References Cited

FOREIGN PATENT DOCUMENTS

| | | | | |
|---|---|---|---|---|
| CN | 101491775 | A | | 7/2009 |
| CN | 102093161 | A | * | 6/2011 |
| CN | 101491775 | B | * | 9/2012 |
| CN | 106866365 | A | | 6/2017 |
| CN | 109232188 | A | | 1/2019 |
| DE | 2809995 | A1 | | 8/2002 |

OTHER PUBLICATIONS

Machine translation of CN101491775B, Sep. 12, 2012, pp. 1-36 (Year: 2012).*

International Search Report for PCT/CN2021/133098 filed on Nov. 25, 2021, 4 pages.

Zhang, Dengqian et al., “Study on NiMo ZrO2—Al2O3 catalysts for ultra deep HDS of diesel”, Industrial Catalysts, Oct. 2008, vol. 16, No. 10, 8 pages.

* cited by examiner

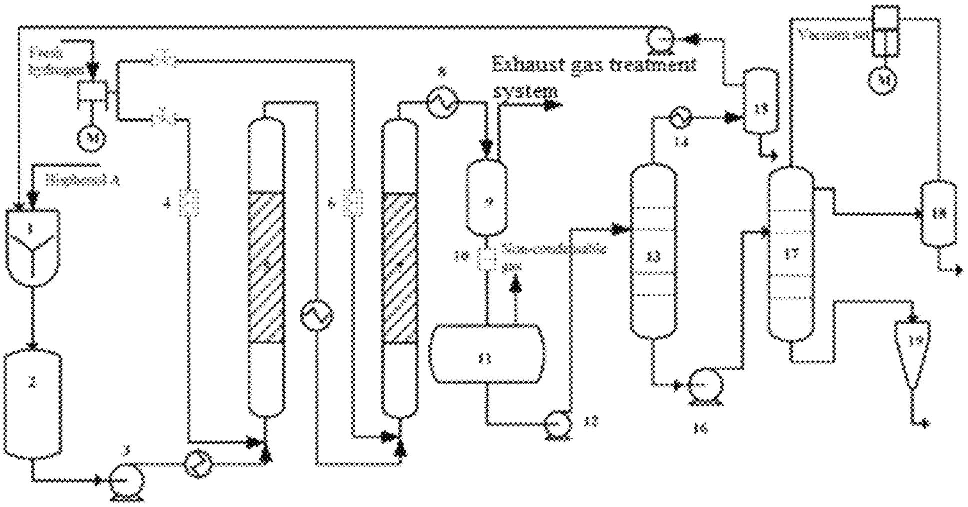
Exhaust gas treatment system

HYDROGENATION CATALYST, PREPARATION METHOD FOR SAME, APPLICATIONS THEREOF, AND HYDROGENATION REACTION METHOD

CROSS REFERENCE TO RELATED APPLICATIONS

This application claims the benefit of Chinese patent application 202011513316.2, filed on Dec. 18, 2020, the contents of which are incorporated herein by reference.

FIELD OF THE INVENTION

The present invention relates to a hydrogenation catalyst, a preparation method for the same, and applications thereof, and further relates to a hydrogenation reaction method employing the hydrogenation catalyst.

BACKGROUND OF THE INVENTION

Hydrogenated bisphenol A (HBPA, CAS: 1980-4-6, $C_{15}H_{28}O_2$) is an alicyclic diol obtained by subjecting two benzene rings in a bisphenol A molecule to hydrogenation saturation, and is one of the key monomers for preparing polymers such as epoxy resin, polycarbonate, polyacrylic resin and unsaturated resin. Compared with bisphenol A, the hydrogenated bisphenol A has significantly improved thermal stability, chemical stability and weather resistance, which is more suitable for outdoor engineering, and more beneficial for human health.

Preparation of the hydrogenated bisphenol A is similar to hydrogenation of a benzene ring, typically using a noble metal catalyst or a nickel-based catalyst. For example, CN1375484A discloses a method for preparing 2,2'-bis(4-hydroxycyclohexyl)propane by hydrogenating 4,4'-dihydroxydiphenylpropane, wherein in the presence of a catalyst comprising ruthenium supported on silica having an acid activity index of 10% or less, a solution of 4,4'-dihydroxydiphenylpropane in a solvent is in contact with hydrogen, the acid activity index being defined as a conversion rate of 2-propanol when a gas flow consisting of 5% by volume of 2-propanol and 95% by volume of helium passes through a fixed bed reactor containing 1.00 g of the catalyst at 250° C. at a helium flow rate of 50 mL/min. The hydrogenation catalyst is improved in preventing by-products generated due to dehydration.

CN106866365A provides a fixed bed hydrogenation process using a noble metal supported catalyst with aluminum oxide modified with alkali metal or phosphorus element as support, one or more of Pd, Ru, and Rh as active component, and trace amount of one or more metal elements of groups VIIB and VIII as an activity improver.

Although the noble metal catalyst shows better catalytic activity in a hydrogenation reaction of bisphenol A, the cost of the noble metal catalyst is high, which is not conducive to the improvement of economy.

In U.S. Pat. No. 2,118,954, a supported nickel-based catalyst is used in liquid phase tank hydrogenation of bisphenol A to prepare hydrogenated bisphenol A at a reaction temperature of 200° C. and a pressure of 10-20 MPa, however, the method has long reaction time and low product yield. Moreover, the nickel-based catalyst in the present invention has major problems of low catalytic activity, high reaction temperature, and difficulty in achieving continuous production.

To sum up, the conventional noble metal hydrogenation catalyst for bisphenol A is high in cost, while the nickel-based catalyst has low catalytic activity, high reaction temperature, and difficulty in achieving continuous production. Therefore, it is necessary to develop a hydrogenation catalyst that is low in cost, high in activity and suitable for the continuous production of hydrogenated bisphenol A.

SUMMARY OF THE INVENTION

The present invention aims to overcome the disadvantages that the existing nickel-based catalysts have low activity in a hydrogenation reaction of bisphenol A, it is necessary to carry out the hydrogenation reaction at a higher temperature, and it is difficult to achieve continuous production, and provide a hydrogenation catalyst which shows a significantly improved catalytic activity in the hydrogenation reaction of bisphenol A, enables the hydrogenation reaction to be carried out at a lower temperature, and can achieve a higher catalytic activity.

According to a first aspect of the present invention, the present invention provides a hydrogenation catalyst, comprising binding agent and active component, wherein the active component comprises nickel element and Group VIB metal element, and the binding agent comprises zirconium oxide and aluminum oxide.

According to a second aspect of the present invention, the present invention provides a preparation method for a hydrogenation catalyst, comprising the following steps of:

(1) contacting precipitating agent with solution comprising nickel compound and zirconium compound, and separating solid phase substance from a mixture resulting from the contacting to obtain a precipitate;

(2) mixing the precipitate with Group VIB metal compound and aluminum-containing compound for shaping to obtain a shaped body, wherein the Group VIB metal compound is Group VIB metal oxide and/or precursor of a Group VIB metal oxide, and the aluminum-containing compound is aluminum oxide and/or precursor of aluminum oxide;

(3) sequentially drying and calcining the shaped body to obtain a catalyst precursor; and (4) contacting the catalyst precursor with reducing agent under conditions of reduction reaction.

According to a third aspect of the present invention, the present invention provides a hydrogenation catalyst prepared by the method in the second aspect of the present invention.

According to a fourth aspect of the present invention, the present invention provides application of the catalyst according to the first or third aspect of the present invention as catalyst for hydrogenation reaction.

According to a fifth aspect of the present invention, the present invention provides a hydrogenation reaction method, comprising contacting a phenolic compound shown in Formula I and hydrogen with a hydrogenation catalyst in the presence of at least one solvent under conditions of hydrogenation reaction, wherein the hydrogenation catalyst is the catalyst according to the first or third aspect of the present invention, (Formula I)

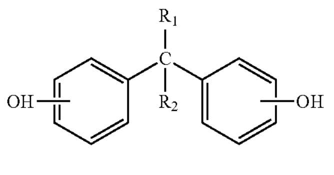

in Formula I, $R_1$ and $R_2$ are the same or different, and are each independently hydrogen atom or $C_1$-$C_5$ alkyl.

The catalyst according to the present invention has nickel as main active component, and thus is low cost. Moreover, the catalyst according to the present invention exhibits an increased catalytic activity in hydrogenation reaction of phenolic compounds and specifically provides an increased low-temperature reaction activity, and can achieve a higher catalytic activity under relatively mild reaction conditions (the reaction temperature is lower than 150° C.) when used as catalyst for the hydrogenation of bisphenol A to prepare hydrogenated bisphenol A.

The catalyst according to the present invention is applicable in a continuous production process, thus implementing the continuous production of hydrogenated bisphenol A product and providing the product with high and stable quality.

BRIEF DESCRIPTION OF DRAWINGS

The FIGURE is used to illustrate a preferred embodiment of hydrogenation reaction method according to the present invention.

DESCRIPTION OF REFERENCE SIGNS

| | |
|---|---|
| 1: | Dissolving tank |
| 2: | Hydrogenation feedstock buffer tank |
| 3: | Metering pump |
| 4: | Flow controller |
| 5: | Main hydrogenation shell and tube reactor |
| 6: | Flow controller |
| 7: | Post-hydrogenation fixed bed reactor |
| 8: | Condenser |
| 9: | High-pressure separation tank |
| 10: | Control valve |
| 11: | Hydrogenation crude product tank |
| 12: | Metering pump |
| 13: | Atmospheric desolvation column |
| 14: | Condenser |
| 15: | Solvent recovery tank |
| 16: | Pump |
| 17: | Vacuum tower |
| 18: | By-product tank |
| 19: | Flaker |

DETAILED DESCRIPTION OF THE EMBODIMENTS

The endpoints and any values of the ranges disclosed herein are not limited to the precise range or value, and these ranges or values should be understood as including values close to these ranges or values. For numerical ranges, the endpoint values of each range, the endpoint values of each range and individual point values, and individual point values may be combined with each other to obtain one or more new numerical ranges, and these numerical ranges should be considered to be specifically disclosed herein.

According to a first aspect of the present invention, the present invention provides a hydrogenation catalyst, comprising binding agent and active component, wherein the active component comprises nickel element and Group VIB metal element, and the binding agent comprises zirconium oxide and aluminum oxide.

According to the catalyst of the present invention, the content of the nickel element is 20-60 wt %, preferably 30-50 wt %, the content of Group VIB metal oxide is 0.1-15 wt %, preferably 0.5-10 wt %, the content of zirconium oxide is 1-40 wt %, preferably 5-30 wt %, and the content of aluminum oxide is 5-70 wt %, preferably 10-64.5 wt % based on the total amount of the catalyst.

In the present invention, nickel in the catalyst is calculated by element. According to the catalyst of the present invention, the content of the nickel element may specifically be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 wt % based on the total amount of the catalyst.

According to the catalyst of the present invention, the content of the Group VIB metal element in the catalyst is calculated by oxide. According to the catalyst of the present invention, the content of the Group VIB metal oxide may be 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9 or 15 wt % based on the total amount of the catalyst. The Group VIB metal element is preferably molybdenum.

According to the catalyst of the present invention, the content of zirconium oxide may specifically be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 wt % based on the total amount of the catalyst.

According to the catalyst of the present invention, the content of aluminum oxide may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 64.5, 65, 66, 67, 68, 69 or 70 wt % based on the total amount of the catalyst.

According to the catalyst of the present invention, the binding agent is preferably zirconium oxide and aluminum oxide.

In the present invention, the catalyst is characterized by X-ray fluorescence spectroscopy.

According to the catalyst of the present invention, a molar ratio of the nickel element to zirconium oxide in the catalyst is preferably 2-21:1, more preferably 2.2-18:1 from the viewpoint of further improving the catalytic activity of the catalyst.

The catalyst according to the present invention has nickel as the active component, and can achieve an increased catalytic activity, in particular a good low-temperature catalytic activity even without introducing noble metal active component in the catalyst. The catalyst according to the present invention preferably does not comprise noble metal element.

According to a second aspect of the present invention, the present invention provides a preparation method for a hydrogenation catalyst, comprising the following steps of:

(1) contacting precipitating agent with solution comprising nickel compound and zirconium compound, and separating solid phase substance from a mixture resulting from the contacting to obtain a precipitate;

(2) mixing the precipitate with Group VIB metal compound and aluminum-containing compound, and drying, calcining and shaping the resulting mixture sequentially to obtain catalyst precursor, wherein the Group VIB metal compound is Group VIB metal oxide and/or precursor of Group VIB metal oxide, and the aluminum-containing compound is aluminum oxide and/or precursor of aluminum oxide; and (3) contacting the catalyst precursor with reducing agent under conditions of reduction reaction.

In the step (1), the nickel compound and the zirconium compound are subjected to a liquid phase precipitation reaction with the precipitating agent to obtain a precipitate comprising nickel and zirconium. The nickel compound and the zirconium compound may be water-soluble compounds capable of undergoing a precipitation reaction. In particular, the nickel compound may be one or two or more selected from the group consisting of nickel sulfate, nickel nitrate, nickel chloride, nickel acetate and nickel formate. The zirconium compound may be one or two or more selected from the group consisting of zirconium sulfate, zirconium nitrate, zirconium oxide and zirconyl nitrate.

In the step (1), solvent of the solution comprising the nickel compound and the zirconium compound is preferably water. The nickel compound and the zirconium compound may be dissolved in water to obtain the solution comprising the nickel compound and the zirconium compound. The concentrations of the nickel compound and the zirconium compound may be conventionally selected.

The precipitating agent may be a substance that enables a precipitation reaction of the nickel compound and the zirconium compound in a liquid phase. Generally, the precipitating agent may be inorganic base, such as one or two or more selected from the group consisting of hydroxide of alkali metal, carbonate of alkali metal and ammonia ($NH_3$). Specific examples of the precipitating agent may include, but are not limited to, one or two or more selected from the group consisting of sodium hydroxide, potassium hydroxide, lithium hydroxide, sodium carbonate, potassium carbonate, and ammonia. In one more preferred embodiment, the precipitating agent is hydroxide of alkali metal and carbonate of alkali metal. In this more preferred embodiment, a molar ratio of the hydroxide of alkali metal to the carbonate of alkali metal is preferably 1:1-5, for example, 1:2-5.

The precipitating agent is preferably dissolved in water in advance to form precipitating agent solution, and the precipitating agent solution is in contact with the solution comprising the nickel compound and the zirconium compound for a precipitation reaction. In one preferred embodiment, the solution comprising the nickel compound and the zirconium compound and the precipitating agent solution are subjected to a co-precipitation reaction in a parallel flow to obtain a precipitate. The specific operating conditions of carrying out the co-precipitation reaction in the parallel flow are not particularly limited in the present invention, and the co-precipitation reaction may be carried out under conventional conditions. In the step (1), the precipitating agent is in contact with the solution comprising the nickel compound and the zirconium compound with stirring for a precipitation reaction.

In the step (1), the precipitation reaction may be carried out under conventional conditions. Specifically, the precipitating agent may be in contact with the solution comprising the nickel compound and the zirconium compound at a temperature of 40-60° C., for example, 40, 41, 42, 43, 44, 45, 46, 47, 48, 49, 50, 51, 52, 53, 54, 55, 56, 57, 58, 59, or 60° C. An end point of a contacting reaction is preferably controlled to have a pH of 11-12, for example, 11.1, 11.2, 11.3, 11.4, 11.5, 11.6, 11.7, 11.8, 11.9 or 12.

In the step (1), the solid phase substance may be separated from a liquid-solid mixture resulting from the contacting by using a conventional method to obtain the precipitate containing nickel and zirconium. In particular, the mixture resulting from the contacting may be filtered, and the solid substance resulting from the filtration may be washed to obtain the precipitate. The washing is based on that ions entrained in the solid substance resulting from the filtration may be substantially removed. Generally, the number of times of the washing may be 3-6 times.

According to the method of the present invention, in the step (2), the precipitate obtained in the step (1) is mixed with the Group VIB metal compound and the aluminium-containing compound.

The Group VIB metal compound is Group VIB metal oxide and/or precursor of a Group VIB metal oxide. The precursor of the Group VIB metal oxide refers to a substance capable of introducing the Group VIB metal oxide into the catalyst. In one preferred embodiment, the Group VIB metal compound is Group VIB metal oxide. According to the method of the present invention, the Group VIB metal may be one or two or more selected from the group consisting of chromium, molybdenum and tungsten. In one preferred embodiment, the Group VIB metal is molybdenum, and the Group VIB metal oxide is preferably oxide of molybdenum, such as molybdenum oxide.

The aluminum-containing compound is aluminum oxide and/or precursor of aluminum oxide. Preferably, the aluminium-containing compound is the precursor of aluminium oxide. More preferably, the aluminium-containing compound is pseudoboehmite.

According to the method of the present invention, in the step (2), the precipitate obtained in the step (1) may be mixed with the Group VIB metal compound and the aluminium-containing compound by using a conventional method. As one preferred example, mixing can be carried out by mixing the precipitate obtained in the step (1) with the Group VIB metal compound and the aluminum-containing compound to be slurried.

In the step (2), the mixture obtained by mixing is sequentially dried and calcined, thereby obtaining a calcined solid substance. The drying may be carried out at a temperature of 80-120° C. The drying may be selected according to the drying temperature. Generally, a duration of the drying may be 4-20 h, for example, 2-20 h. The calcining may be carried out at a temperature of 400-600° C., and a duration of the calcining may be 2-10 h, preferably 2-5 h.

In the step (2), the solid substance obtained by calcining is shaped to obtain the catalyst precursor. A shaping method is not particularly limited in the present invention, and the shaping can be performed by a conventional method. In particular, the shaping method may be one or a combination of two or more of extrusion and tabletting.

According to the method of the present invention, in the step (3), the catalyst precursor obtained in the step (2) is in contact with the reducing agent under conditions of the reduction reaction to activate the catalyst precursor, thereby obtaining the catalyst according to the present invention. In one preferred embodiment, the reducing agent is hydrogen. According to this preferred embodiment, the catalyst precursor may be activated in a reducing atmosphere. The reducing atmosphere may be a hydrogen atmosphere or a mixed atmosphere formed by hydrogen and a diluent gas, and the diluent gas may be nitrogen and/or a Group zero gas (e.g. helium and argon). When the mixed atmosphere formed by hydrogen and the diluent gas is used, the content of hydrogen in the mixed atmosphere is based on being sufficient to activate the catalyst precursor. Generally, the content of hydrogen in the mixed atmosphere may be 1-30% by volume, preferably 2-25% by volume, more preferably 5-20% by volume, for example, 5-15% by volume. In the step (3), the catalyst precursor may be in contact with the reducing agent at a temperature of 400-460° C. The contacting may be carried out under a pressure of 0.1-5 MPa, the pressure being gauge pressure. In the step (3), a duration of the contacting may be 2-15 h, preferably 4-10 h.

According to the preparation method of the present invention, the usage amounts of the nickel compound, the zirconium compound, the Group VIB metal compound and the aluminum-containing compound may be selected according to the intended catalyst composition. In one preferred embodiment, the nickel compound, the zirconium compound, the Group VIB metal compound and the aluminum-containing compound are used in amounts such that the content of the nickel element is 20-60 wt %, preferably 30-50 wt %, the content of the Group VIB metal oxide is 0.1-15 wt %, preferably 0.5-10 wt %, the content of zirconium oxide is 1-40 wt %, preferably 5-30 wt %, and the content of aluminum oxide is 5-70 wt %, preferably 10-64.5 wt % based on the total amount of the finally prepared catalyst. According to this preferred embodiment, from the viewpoint of further improving the catalytic activity of the finally prepared catalyst, the nickel compound and the zirconium compound are used in amounts such that a molar ratio of the nickel element to zirconium oxide is preferably 2-21:1, more preferably 2.2-18:1 based on the total amount of the finally prepared catalyst. A method for determining the usage amounts of the nickel compound, the zirconium compound, the Group VIB metal compound and the aluminum-containing compound according to the intended catalyst composition is well known to those skilled in the art, which will be not described in detail herein.

According to a third aspect of the present invention, the present invention provides a hydrogenation catalyst prepared by the method in the second aspect of the present invention.

According to a fourth aspect of the present invention, the present invention provides application of the catalyst according to the first or third aspect of the present invention as a catalyst for a hydrogenation reaction.

The hydrogenation reaction may be, for example, a hydrogenation reaction subjecting benzene ring to hydrogenation saturation, for example, hydrogenation reaction subjecting phenolic compounds to hydrogenation saturation to corresponding cycloaliphatic alcohols.

According to a fifth aspect of the present invention, the present invention provides a hydrogenation reaction method, comprising contacting a phenolic compound shown in Formula I and hydrogen with a hydrogenation catalyst in hydrogenation reaction zone in the presence of at least one solvent under the conditions of hydrogenation reaction, wherein the hydrogenation catalyst is the catalyst according to the first or third aspect of the present invention.

The hydrogenation catalyst and the preparation method therefor have been described in detail above and will not be described in detail here.

According to the hydrogenation reaction method of the present invention, the phenolic compound is a compound shown in Formula I, (Formula I)

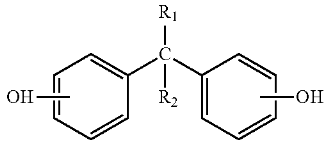

in Formula I, $R_1$ and $R_2$ are the same or different, and are each hydrogen atom or $C_1$-$C_5$ alkyl. Specific examples of the $C_1$-$C_5$ alkyl may include, but are not limited to, methyl, ethyl, n-propyl, isopropyl, n-butyl, sec-butyl, isobutyl, tert-butyl, n-pentyl or isopentyl.

The phenolic compound is preferably 2,2-bis(4-hydroxyphenyl)propane (i.e., bisphenol A) and/or bis(4-hydroxyphenyl)methane (i.e., bisphenol F).

According to the hydrogenation reaction method of the present invention, the phenolic compound and the hydrogen are in contact with the hydrogenation catalyst in the presence of at least one solvent. The solvent may be one or two or more selected from the group consisting of alcohol-type solvent, ester-type solvent, and alcohol ether-type solvent. The alcohol-type solvent may be $C_1$-$C_5$ fatty alcohol. The ester-type solvent may be an acetate-type solvent. The alcohol ether-type solvent may be monoether of aliphatic glycol and/or diether of aliphatic glycol. Specific examples of the solvent may include, but are not limited to, one or a combination of two or more selected from the group consisting of methanol, ethanol, n-propanol, isopropanol, n-butanol, isobutanol, tert-butanol, methyl acetate, ethyl acetate, n-propyl acetate, isopropyl acetate, n-butyl acetate, sec-butyl acetate, ethylene glycol monomethyl ether, and ethylene glycol dimethyl ether. The amount of the solvent used can be conventionally selected. Generally, the solvent is used in an amount such that the content of the phenolic compound is 5-30 wt % based on the total amount of the solvent and the phenolic compound.

According to the hydrogenation reaction method of the present invention, the hydrogen and the phenolic compound may be separately fed into the hydrogenation reaction zone to be in contact with the hydrogenation catalyst for reaction. Preferably, the phenolic compound and the hydrogen are mixed to be fed into the hydrogenation reaction zone to be in contact with the hydrogenation catalyst.

In one preferred embodiment, the phenolic compound, the hydrogen, and the solvent are mixed to form a feedstock mixture, and the feedstock mixture is fed into the hydrogenation reaction zone to be in contact with the hydrogenation catalyst for a hydrogenation reaction.

In this preferred embodiment, hydrogen may be mixed with a feedstock solution comprising the phenolic compound and the solvent by using a conventional method to obtain the feedstock mixture. For example, hydrogen may be mixed with the feedstock solution comprising the phenolic compound and the solvent in a mixer, wherein the mixer may be one or a combination of two or more of a dynamic mixer and a static mixer. The static mixer achieves uniform mixing of gas and liquid by changing a flow state of a fluid, and may be specifically, but is not limited to, one or a combination of two or more selected from the group consisting of SV-type static mixer, SK-type static mixer, SX-type static mixer, SH-type static mixer and SL-type static mixer. The dynamic mixer may be a variety of mixing devices that achieve uniform mixing of gas and liquid through the movement of moving parts, such as common various parts having a stirring function.

In one preferred embodiment, hydrogen is injected into the feedstock solution through a gas-liquid mixer, thereby obtaining the feedstock mixture, wherein the gas-liquid mixer comprises at least one liquid channel for accommodating the feedstock solution and at least one gas channel for accommodating the hydrogen, the liquid channel and the gas channel are adjoined by a member, and at least part of the member is a perforated area through which the hydrogen is injected into the feedstock solution. In the present invention, the term "liquid channel" refers to a space capable of accommodating a liquid phase stream; and the term "gas channel" refers to a space capable of accommodating hydrogen.

At least part of the member is a perforated area which extends along the length of the member. Preferably, the perforated area covers the entire member (i.e. the liquid channel and the gas channel are adjoined by a member having pores with an average pore size being nano-scaled, and the hydrogen is injected into the liquid phase stream through the pores). The perforated area has pores with an average pore size being nano-scaled such that hydrogen is injected into the liquid phase stream through the pores with the average pore size being nano-scaled.

In this preferred embodiment, the pores in the perforated area may be micro-pores and/or nano-pores. In the present invention, the term "micro-pores" refers to pores having an average pore size of more than 1000 nm, and the micro-pores preferably have an average pore size of not more than 600 μm, more preferably not more than 500 μm. In the present invention, the term "nano-pores" refers to pores having an average pore size of not more than 1000 nm, such as pores having an average pore size of 1 nm to 1000 nm. More preferably, the pores in the perforated area are nano-pores. Further preferably, the pores in the perforated area have an average pore size of 50 nm to 500 nm. The average pore size is determined by scanning electron microscopy.

The member may be one or a combination of two or more selected from the group consisting of porous membrane, porous plate, and porous pipe. The porous pipe means that a wall of a channel is porous. An inner surface and/or an outer surface of the porous pipe may be attached with a porous membrane, in this way, a pore size of pores in the pipe can be adjusted, for example, the pores in the wall of the pipe may be micro-pores, and pores in the porous membrane attached to the inner surface and/or the outer surface of the pipe may be nano-pores, and in the present invention, the pipe of which the inner surface and/or the outer surface are/is attached with the porous membrane in which pores are nano-pores is also considered to be that pores in the perforated area are nano-pores. As an example of a pipe having a porous membrane, the porous pipe may be a membrane pipe. The number of channels in the porous pipe is not particularly limited, and generally, the number of the channels in the porous pipe may be 4-20.

The gas-liquid mixer may be disposed at an inlet end of the reactor such that the feedstock mixture output from the gas-liquid mixer is directly fed into the reactor.

According to the hydrogenation reaction method of the present invention, the amount of hydrogen injected may be selected according to the content of the phenolic compound in the feedstock solution, which is based on that being sufficient to hydrogenate the phenolic compound, and is, for example, based on that the phenolic compound is hydrogenated to a corresponding cycloaliphatic alcohol. Generally, a molar ratio of the amount of hydrogen injected to the phenolic compound in the feedstock solution may be 4-10:1.

According to the hydrogenation reaction method of the present invention, by using the hydrogenation catalyst of the present invention, even if hydrogen and the phenolic compound are in contact with the hydrogenation catalyst for reaction at a relatively low temperature, the phenolic compound can be converted at a relatively high conversion rate, and the selectivity to the corresponding cycloaliphatic alcohol can be remarkably improved. In particular, the hydrogen and the phenolic compound may be in contact with the hydrogenation catalyst at a temperature of 50-140° C.

According to the hydrogenation reaction method of the present invention, hydrogen and the phenolic compound may be in contact with the hydrogenation catalyst under a relatively low pressure. In particular, a pressure within the hydrogenation reaction zone may be 1-6 MPa in terms of a gauge pressure.

The method according to the present invention may be carried out continuously or intermittently. The catalyst used in the method according to the present invention has an increased catalytic activity and is particularly suitable for carrying out a hydrogenation reaction by a continuous process. According to the method of the present invention, the hydrogenation reaction is preferably carried out in one or a combination of both of fixed bed reactor and tubular reactor. In the present invention, the fixed bed reactor refers to a reactor in which catalyst is packed in reaction zone of the reactor to form catalyst bed layer (ratio of inner diameter of the catalyst bed layer to total height of the catalyst packed within the reactor is typically greater than 1, preferably 3-10:1), and the tubular reactor refers to a reactor in which two or more reaction tubes are arranged inside the reactor, and catalyst is packed in the reaction tubes (ratio of inner diameter of each reaction tube to total height of the catalyst packed in the reaction tube is typically less than 1).

According to the hydrogenation reaction method of the present invention, the number of the hydrogenation reaction zone may be one or two or more. The two or more hydrogenation reaction zones may be connected in series or in parallel or in a combination of series and parallel. When there are two or more hydrogenation reactants, the hydrogenation reaction zones may be located in different regions of a same reactor or in different reactors.

According to the hydrogenation reaction method of the present invention, from the viewpoint of further improving the reaction effect, in one preferred embodiment, the contacting of the phenolic compound and the hydrogen with the hydrogenation catalyst comprises first contacting and second contacting, wherein in the first contacting, the phenolic compound and the hydrogen are in contact with first portion of the hydrogenation catalyst under the conditions of first hydrogenation reaction to obtain first contacted product mixture; and in the second contacting, the first contacted product mixture and supplemental hydrogen are in contact with second portion of the hydrogenation catalyst under the conditions of second hydrogenation reaction to obtain second contacted product mixture.

The hydrogenation catalyst employed according to the method of the present invention has an increased low-temperature reaction activity, and the phenolic compound as feedstock for the hydrogenation reaction can be effectively converted at a high conversion rate, and high product selectivity can be obtained even when the reaction is carried out at a lower temperature. According to this preferred embodiment, the first contacting may be carried out at a temperature of 60-90° C., for example, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90° C. According to this preferred embodiment, the second contacting may be carried out at a temperature of 80-140° C., for example, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140° C. According to this preferred embodiment, the temperature of the second contacting is preferably not lower than the temperature of the first contacting, so that further improved feedstock conversion and product selectivity can be obtained. More preferably, the temperature of the second contacting is 20-50° C. higher than the temperature of the first contacting.

A molar ratio of the phenolic compound to the hydrogen (i.e., the hydrogen employed in the first contacting) to the supplemental hydrogen (i.e., the hydrogen employed in the second contacting) in the first contacting and the second contacting is preferably 1:4-6:1-4.

In the first contacting and the second contacting, pressures may be the same or different, and each may be in the range of 1-5 MPa, the pressures being gauge pressures.

Preferably, a weight hourly space velocity in the first contacting is 1-6 $h^{-1}$, for example, 1-5 $h^{-1}$, and a weight hourly space velocity in the second contacting is 0.5-3 $h^{-1}$, the weight hourly space velocities being in terms of the phenolic compound.

The first contacting and the second contacting may employ same hydrogenation catalyst or may employ different hydrogenation catalysts.

According to this preferred embodiment, the first contacting is preferably carried out in tubular reactor through which the phenolic compound and the solvent preferably flow upwards. According to this preferred embodiment, the second contacting is preferably carried out in fixed bed reactor through which the first contacted product mixture preferably passes in an upward flow.

According to the hydrogenation reaction method of the present invention, a reaction mixture resulting from the hydrogenation reaction may be separated by using a conventional method to obtain a hydrogenation product. In particular, a solvent may be removed from the reaction mixture resulting from the hydrogenation reaction, thereby separating the hydrogenation product and recovering the solvent, preferably recycling at least part of the recovered solvent for the hydrogenation reaction. The solvent may be separated from the reaction mixture resulting from the hydrogenation reaction by distillation to obtain the hydrogenation product. The distillation may be atmospheric distillation, reduced pressure distillation, or a combination thereof. In one preferred embodiment, the reaction mixture resulting from the hydrogenation reaction is subjected to atmospheric distillation followed by reduced pressure distillation to obtain the hydrogenation product and to recover the solvent. The atmospheric distillation may be carried out in an atmospheric desolvation column, and the atmospheric distillation may be carried out at a distillation column bottom temperature of 200-240° C., preferably 210-230° C. The reduced pressure distillation preferably employs wiped film distillation column. The reduced pressure distillation may be carried out at a column bottom temperature of 180-220° C., and a pressure at the top of the distillation column is preferably controlled to be −0.08 MPa to −0.1 MPa during the reduced pressure distillation.

The FIGURE shows a preferred embodiment of a hydrogenation reaction method according to the present invention. This preferred embodiment is described below with reference to the FIGURE.

Bisphenol A is dissolved with solvent from solvent tank 15 in a dissolving tank 1 with stirring to form a feedstock solution comprising 5-30 wt % of bisphenol A, the feedstock solution is fed into hydrogenation feedstock buffer tank 2, and metered and pressurized through metering pump 3, and the pressurized feedstock solution is mixed with high pressure hydrogen metered through flow controller 4 in a pipe, and then the mixture enters main hydrogenation tubular reactor 5 from bottom to top to be in contact with hydrogenation catalyst packed in tubes of the main hydrogenation tubular reactor for main hydrogenation reaction. An outlet mixture of the main hydrogenation tubular reactor 5 is mixed with high-pressure supplemental hydrogen metered through flow controller 6 in pipe, and then the mixture enters post-hydrogenation fixed bed reactor 7 from bottom to top to be in contact with hydrogenation catalyst packed in the post-hydrogenation fixed bed reactor 7 for hydrogenation reaction. An outlet mixture of the post-hydrogenation fixed bed reactor 7 is cooled by condenser 8, and enters high-pressure separation tank 9 for gas-liquid separation, after a small amount of vaporized solvent entrained in the separated hydrogen is removed, the separated hydrogen enters hydrogen exhaust gas treatment system, and the separated hydrogenation product solution enters hydrogenation crude product tank 11 through control valve 10.

The hydrogenation product solution in the hydrogenation crude product tank 11 is metered by metering pump 12 to be fed into atmospheric desolvation column 13 to remove solvent. The removed solvent is cooled by condenser 14, and collected to be fed into solvent recovery tank 15. The recovered solvent in the solvent recovery tank 15 can be recycled. A material at the bottom of the atmospheric desolvation column 13 enters vacuum tower 17 via pump 16 for further removal of hydrogenation by-products, wherein the vacuum tower 17 is preferably wiped film distillation column, the removed hydrogenation by-products are fed into by-product tank 18, and the hydrogenation product with the solvent and the by-products removed enters flaker 19 for flaking to obtain hydrogenated bisphenol A product.

The present invention is described in detail below with reference to examples, but the scope of the present invention is not thereby limited.

In the following Examples and Comparative examples, the pressures are in terms of gauge pressures unless otherwise specified.

In the following Examples and Comparative examples, a composition of a reaction solution output from a reactor was determined by gas chromatography, and the feedstock conversion and product selectivity were calculated according to the determined composition data by using the following formulae, Feedstock conversion=(the molar amount of feedstocks added−the molar amount of the remaining feedstocks)/the molar amount of feedstocks added×100%; and Product selectivity=the molar amount of a product produced by a reaction/(the molar amount of feedstocks added−the molar amount of the remaining feedstocks)×100%.

Preparation examples 1-9 were used to prepare the hydrogenation catalyst according to the present invention.

Preparation Example 1

In this example, a hydrogenation catalyst A comprises 30 wt % of nickel element, 5 wt % of molybdenum oxide ($MoO_3$), 20 wt % of zirconium oxide, and 45 wt % of aluminum oxide based on the total amount of the catalyst. The hydrogenation catalyst A was prepared by using the following method:

(1) An aqueous solution comprising nickel nitrate and zirconium nitrate and an aqueous solution comprising sodium hydroxide and sodium carbonate (a molar ratio of sodium hydroxide to sodium carbonate was 1:2) were subjected to co-precipitation in a parallel flow at 40° C. with stirring, an endpoint pH was controlled to be 11, the resulting reaction mixture was filtered, and a collected solid matter was washed with deionized water for 5 times to obtain a nickel zirconium co-precipitate.

(2) The nickel zirconium co-precipitate was mixed with molybdenum oxide and pseudoboehmite to be slurried, and then dried at 120° C. for 6 h, followed by calcination at 500° C. for 3 h, and powder obtained by calcination was subjected to tabletting forming to obtain a catalyst precursor.

(3) The catalyst precursor was subjected to activation treatment in a mixed atmosphere of hydrogen and nitrogen (the hydrogen content was 10% by volume) to obtain the hydrogenation catalyst A according to the present invention, wherein the temperature was 430° C., the pressure was 0.2 MPa, and the time was 10 h.

Preparation Example 2

In this preparation example, a hydrogenation catalyst B comprises 50 wt % of nickel element, 0.5 wt % of molybdenum oxide, 30 wt % of zirconium oxide, and 19.5 wt % of aluminum oxide based on the total amount of the catalyst. The hydrogenation catalyst B was prepared by using the following method:

(1) An aqueous solution comprising nickel chloride and zirconium chloride and an aqueous solution comprising potassium hydroxide and sodium carbonate (a molar ratio of potassium hydroxide to sodium carbonate was 1:3) were subjected to co-precipitation in a parallel flow at 60° C. with stirring, an endpoint pH was controlled to be 12, the resulting reaction mixture was filtered, and a collected solid matter was washed with deionized water for 6 times to obtain a nickel zirconium co-precipitate.

(2) The nickel zirconium co-precipitate was mixed with molybdenum oxide and pseudoboehmite to be slurried, and then dried at 100° C. for 6 h, followed by calcination at 400° C. for 5 h, and powder obtained by calcination was subjected to tabletting forming to obtain a catalyst precursor.

(3) The catalyst precursor was subjected to activation treatment in a mixed atmosphere of hydrogen and nitrogen (the hydrogen content was 15% by volume) to obtain the hydrogenation catalyst B according to the present invention, wherein the temperature was 420° C., the pressure was 5 MPa, and the time was 4 h.

Comparative Preparation Example 1

In this comparative preparation example, a hydrogenation catalyst CD1 comprises 50 wt % of nickel element, 30 wt % of zirconium oxide, and 20 wt % of aluminum oxide based on the total amount of the catalyst.

A hydrogenation catalyst was prepared by the same method as that in Preparation example 2, except that molybdenum oxide was not used in the step (2), thereby preparing the hydrogenation catalyst CD1.

Preparation Example 3

In this preparation example, a hydrogenation catalyst C comprises 40 wt % of nickel element, 10 wt % of molybdenum oxide, 5 wt % of zirconium oxide, and 45 wt % of aluminum oxide based on the total amount of the catalyst. The hydrogenation catalyst C was prepared by using the following method:

(1) An aqueous solution comprising nickel sulfate and zirconium sulfate and an aqueous solution comprising potassium hydroxide and potassium carbonate (a molar ratio of potassium hydroxide to potassium carbonate was 1:5) were subjected to co-precipitation in a parallel flow at 50° C. with stirring, an endpoint pH was controlled to be 11.2, the resulting reaction mixture was filtered, and a collected solid matter was washed with deionized water for 3 times to obtain a nickel zirconium co-precipitate.

(2) The nickel zirconium co-precipitate was mixed with molybdenum oxide and pseudoboehmite to be slurried, and then dried at 120° C. for 15 h, followed by calcination at 550° C. for 3 h, and powder obtained by calcination was subjected to tabletting forming to obtain a catalyst precursor.

(3) The catalyst precursor was subjected to activation treatment in a mixed atmosphere of hydrogen and nitrogen (the hydrogen content was 5% by volume) to obtain the hydrogenation catalyst C according to the present invention, wherein the temperature was 460° C., the pressure was 0.1 MPa, and the time was 10 h.

Comparative Preparation Example 2

In this comparative preparation example, a hydrogenation catalyst CD2 comprises 40 wt % of nickel element, 10 wt % of molybdenum oxide, and 50 wt % of aluminum oxide based on the total amount of the catalyst. The hydrogenation catalyst CD2 was prepared by using the following method: a hydrogenation catalyst was prepared by the same method as that in Preparation example 3, except that zirconium sulfate was not used in the step (1), thereby preparing the hydrogenation catalyst CD2.

Comparative Preparation Example 3

In this comparative preparation example, a hydrogenation catalyst CD3 comprises 40 wt % of nickel element, 10 wt % of molybdenum oxide, 5 wt % of silicon oxide, and 45 wt % of aluminum oxide based on the total amount of the catalyst. The hydrogenation catalyst CD3 was prepared by using the following method: a hydrogenation catalyst was prepared by the same method as that in Preparation example 3, except that zirconium sulfate was replaced with an equal amount of sodium silicate, thereby preparing the hydrogenation catalyst CD3.

Preparation Example 4

In this preparation example, a hydrogenation catalyst D comprises 35 wt % of nickel element, 4 wt % of molybdenum oxide, 30 wt % of zirconium oxide, and 31 wt % of aluminum oxide based on the total amount of the catalyst. The hydrogenation catalyst D was prepared by using the following method:

(1) An aqueous solution comprising nickel formate and zirconyl nitrate and an aqueous solution comprising sodium hydroxide and potassium carbonate (a molar ratio of sodium hydroxide to potassium carbonate was 1:4) were subjected to co-precipitation in a parallel flow at 50° C. with stirring, an endpoint pH was controlled to be 11.5, the resulting reaction mixture was filtered, and a collected solid matter was washed with deionized water for three times to obtain a nickel zirconium co-precipitate.

(2) The nickel zirconium co-precipitate was mixed with molybdenum oxide and pseudoboehmite to be slurried, and then dried at 80° C. for 20 h, followed by calcination at 600° C. for 2 h, and powder obtained by calcination was subjected to tabletting forming to obtain a catalyst precursor.

(3) The catalyst precursor was subjected to activation treatment in a mixed atmosphere of hydrogen and nitrogen (the hydrogen content was 5% by volume) to obtain the hydrogenation catalyst D according to the present invention, wherein the temperature was 460° C., the pressure was 5 MPa, and the time was 4 h.

Preparation Example 5

In this preparation example, a hydrogenation catalyst E comprises 50 wt % of nickel element, 0.3 wt % of molybdenum oxide, 30 wt % of zirconium oxide, and 19.7 wt % of aluminum oxide based on the total amount of the catalyst. The hydrogenation catalyst E was prepared by using the following method: a hydrogenation catalyst was prepared by the same method as that in Preparation example 2, except that the amount of molybdenum oxide used in the step (2) was reduced, thereby preparing the hydrogenation catalyst E.

Preparation Example 6

In this preparation example, a hydrogenation catalyst F comprises 55 wt % of nickel element, 0.5 wt % of molybdenum oxide, 30 wt % of zirconium oxide, and 14.5 wt % of aluminum oxide based on the total amount of the catalyst. The hydrogenation catalyst F was prepared by using the following method: a hydrogenation catalyst was prepared by the same method as that in Preparation example 2, except that the amount of nickel chloride used in the step (1) was increased, thereby preparing the hydrogenation catalyst F.

Preparation Example 7

In this preparation example, a hydrogenation catalyst G comprises 25 wt % of nickel element, 5 wt % of molybdenum oxide, 20 wt % of zirconium oxide, and 50 wt % of aluminum oxide based on the total amount of the catalyst. The hydrogenation catalyst G was prepared by using the following method: a hydrogenation catalyst was prepared by the same method as that in Preparation example 1, except that the amount of nickel nitrate used in the step (1) was reduced, thereby preparing the hydrogenation catalyst G.

Preparation Example 8

In this preparation example, a hydrogenation catalyst H comprises 40 wt % of nickel element, 10 wt % of molybdenum oxide, 3 wt % of zirconium oxide, and 47 wt % of aluminum oxide based on the total amount of the catalyst. The hydrogenation catalyst H was prepared by using the following method: a hydrogenation catalyst was prepared by the same method as that in Preparation example 3, except that the amount of zirconium sulfate used in the step (1) was reduced, thereby preparing the hydrogenation catalyst H.

Preparation Example 9

In this preparation example, a hydrogenation catalyst I comprises 35 wt % of nickel element, 4 wt % of molybdenum oxide, 35 wt % of zirconium oxide, and 26 wt % of aluminum oxide based on the total amount of the catalyst. The hydrogenation catalyst I was prepared by using the following method: a hydrogenation catalyst was prepared by the same method as that in Preparation example 4, except that the amount of zirconyl nitrate used in the step (1) was increased, thereby preparing the hydrogenation catalyst I.

Examples 1-13 served to illustrate the hydrogenation reaction method according to the present invention.

In Examples 1-13, hydrogenated bisphenol A was prepared by hydrogenation of bisphenol A by using the conditions listed in Tables 1-2 referring to the manner shown in the FIGURE. A specific process flow was described below:

(1) Firstly, an outlet head was installed at the bottom of a reactor, inert porcelain balls were charged on the outlet head for supporting and material preheating, and then hydrogenation catalyst was charged on the porcelain balls in a random stack, and finally, inert porcelain balls were charged at the upper part of bed layer, and a reactor top head was installed.

(2) Bisphenol A was dissolved with solvent from solvent tank 15 in dissolving tank 1 with stirring to form a feedstock solution comprising 5-30 wt % of bisphenol A, the feedstock solution was fed into hydrogenation feedstock buffer tank 2, and metered and pressurized through metering pump 3, and the pressurized feedstock solution was mixed with high pressure hydrogen metered through flow controller 4 in pipe, and then the mixture entered main hydrogenation tubular reactor 5 from bottom to top to be in contact with a hydrogenation catalyst packed in tubes of the main hydrogenation tubular reactor for a main hydrogenation reaction. An outlet mixture of the main hydrogenation tubular reactor 5 was mixed with high-pressure supplemental hydrogen metered through flow controller 6 in pipe, and then the mixture entered post-hydrogenation fixed bed reactor 7 from bottom to top to be in contact with hydrogenation catalyst packed in the post-hydrogenation fixed bed reactor 7 for hydrogenation reaction. An outlet mixture of the post-hydrogenation fixed bed reactor 7 was cooled by condenser 8, and entered high-pressure separation tank 9 for gas-liquid separation, after a small amount of vaporized solvent entrained in the separated hydrogen was removed, the separated hydrogen entered a hydrogen exhaust gas treatment system, and a separated hydrogenation product solution entered hydrogenation crude product tank 11 through control valve 10.

Specific hydrogenation reaction conditions and reaction results are listed in Table 1, wherein ① is sec-butyl acetate, ② is isopropyl acetate, ③ is n-propanol, ④ is n-butanol, ⑤ is ethylene glycol monomethyl ether, and ⑥ is ethylene glycol dimethyl ether in Table 1.

(3) The hydrogenation product solution in the hydrogenation crude product tank was metered by metering pump 12 to be fed into atmospheric desolvation column 13 to remove solvent. The removed solvent was cooled by condenser 14, and collected to be fed into solvent recovery tank 15. The recovered solvent in the solvent recovery tank 15 may be recycled. A material at the bottom of the atmospheric desolvation column 13 entered vacuum tower 17 via pump 16 for further removal of hydrogenation by-products, wherein the vacuum tower 17 was a wiped film distillation column, the removed hydrogenation by-products were fed into by-product tank 18, and the hydrogenation product with the solvent and the by-products removed entered flaker 19 for flaking to obtain a hydrogenated bisphenol A product.

The operating conditions of the desolvation column 13 and the vacuum tower are listed in Table 2.

Comparative Examples 1-3

A hydrogenation reaction was carried out by the same method as that in Examples 1-13, except that the hydrogenation catalysts prepared in Comparative preparation examples 1-3 were respectively used, and the step (3) was not carried out, and specific operating conditions and reaction results are listed in Table 1.

TABLE 1

| | Main hydrogenation reaction | | | | | | |
|---|---|---|---|---|---|---|---|
| Example | Catalyst | Solvent | Concentration % | Temperature ° C. | Pressure MPa | Space velocity $h^{-1}$ | Hydrogen to phenol ratio mol |
| Example 1 | Preparation example 1 | ① | 15 | 70 | 4 | 5 | 4.8 |
| Example 2 | Preparation example 2 | ② | 5 | 60 | 5 | 1 | 5.0 |
| Example 3 | Preparation example 2 | ③ | 30 | 90 | 1 | 6 | 6.0 |
| Example 4 | Preparation example 4 | ④ | 20 | 80 | 3 | 2.9 | 5.0 |
| Example 5 | Preparation example 3 | ⑤ | 25 | 85 | 2 | 4 | 5.5 |
| Example 6 | Preparation example 1 | ⑥ | 15 | 75 | 4.5 | 4.8 | 5.2 |
| Example 7 | Preparation example 7 | Same as those in Example 1 | | | | | |
| Example 8 | Preparation example 2 | Same as those in Example 2 | | | | | |
| Comparative example 1 | Comparative preparation example 1 | Same as those in Example 2 | | | | | |
| Example 9 | Preparation example 5 | Same as those in Example 2 | | | | | |
| Example 10 | Preparation example 6 | Same as those in Example 2 | | | | | |
| Comparative example 2 | Comparative preparation example 2 | Same as those in Example 5 | | | | | |
| Comparative example 3 | Comparative preparation example 3 | Same as those in Example 5 | | | | | |
| Example 11 | Preparation example 8 | Same as those in Example 5 | | | | | |
| Example 12 | Preparation example 4 | Same as those in Example 5 | | | | | |
| Example 13 | Preparation example 9 | Same as those in Example 4 | | | | | |

| | Post-hydrogenation reaction | | | | | Analytical data | |
|---|---|---|---|---|---|---|---|
| Example | Catalyst | Temperature ° C. | Pressure MPa | Space velocity $h^{-1}$ | Hydrogen to phenol ratio mol | Conversion % | Selectivity % |
| Example 1 | Preparation example 1 | 90 | 4 | 1.3 | 3.5 | 100 | 98.7 |
| Example 2 | Preparation example 3 | 80 | 5 | 0.5 | 1.2 | 100 | 98.9 |
| Example 3 | Preparation example 1 | 140 | 1 | 3 | 4.0 | 100 | 97.1 |
| Example 4 | Preparation example 3 | 110 | 3 | 2 | 1.8 | 100 | 97.2 |
| Example 5 | Preparation example 3 | 120 | 2 | 1 | 2.4 | 100 | 98.0 |
| Example 6 | Preparation example 3 | 100 | 4.5 | 1.8 | 1.6 | 100 | 97.8 |
| Example 7 | Preparation example 7 | Same as those in Example 1 | | | | 95 | 90.5 |

TABLE 1-continued

| | | | | |
|---|---|---|---|---|
| Example 8 | Preparation example 2 | Same as those in Example 2 | 100 | 97.8 |
| Comparative example 1 | Comparative preparation example 1 | Same as those in Example 2 | 83 | 80.1 |
| Example 9 | Preparation example 5 | Same as those in Example 2 | 93 | 91.3 |
| Example 10 | Preparation example 6 | Same as those in Example 2 | 97 | 95.4 |
| Comparative example 2 | Comparative preparation example 2 | Same as those in Example 5 | 87 | 85.5 |
| Comparative example 3 | Comparative preparation example 3 | Same as those in Example 5 | 88 | 84.9 |
| Example 11 | Preparation example 8 | Same as those in Example 5 | 95 | 92.3 |
| Example 12 | Preparation example 4 | Same as those in Example 4 | 99 | 97.3 |
| Example 13 | Preparation example9 | Same as those in Example 4 | 97 | 94.8 |

TABLE 2

| | Desolvation column | | | By-product removal column | | |
|---|---|---|---|---|---|---|
| Example | Column top temperature ° C. | Column bottom temperature ° C. | Pressure MPa | Temperature ° C. | Pressure MPa | Product purity % |
| Example 1 | 115 | 225 | Atmospheric pressure | 180 | −0.08 | 98.0 |
| Example 2 | 93 | 228 | Atmospheric pressure | 190 | −0.09 | 98.3 |
| Example 3 | 86 | 220 | Atmospheric pressure | 210 | −0.1 | 98.2 |
| Example 4 | 118 | 225 | Atmospheric pressure | 220 | −0.08 | 98.1 |
| Example 5 | 127 | 223 | Atmospheric pressure | 195 | −0.09 | 98.2 |
| Example 6 | 129 | 227 | Atmospheric pressure | 200 | −0.09 | 98.1 |

As can be seen from the data of Table 1, the hydrogenation catalyst according to the present invention exhibits an increased catalytic activity in a hydrogenation reaction of bisphenol A, and a good catalytic effect can be obtained even if the hydrogenation reaction is carried out at a lower temperature. The results in Tables 1 and 2 also demonstrate that the hydrogenation catalyst according to the present invention is applicable in a continuous production process, and a hydrogenated bisphenol A product with stable quality can be prepared.

Preferred embodiments of the present invention are described in detail above, but the present invention is not limited thereto. Within the scope of the technical idea of the present invention, many simple variations can be made to the technical solution of the present invention, comprising combinations of the technical features in any other suitable manner, and these simple variations and combinations should also be regarded as the contents disclosed in the present invention, and all fall within the protection scope of the present invention.

The invention claimed is:

1. A hydrogenation reaction method, comprising contacting a phenolic compound shown in Formula I and hydrogen with a hydrogenation catalyst in the presence of at least one solvent under conditions of hydrogenation reaction, (Formula I)

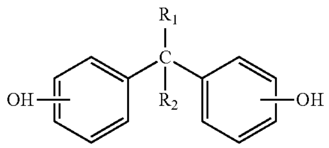

wherein in Formula I, $R_1$ and $R_2$ are the same or different, and are each independently a hydrogen atom or $C_1$-$C_5$ alkyl, the hydrogenation catalyst comprises a binding agent and an active component, wherein the active component comprises nickel element and Group VIB metal element, and the binding agent comprises zirconium oxide and aluminum oxide.

2. The method according to claim 1, wherein the contacting comprises a first contacting and a second contacting, wherein in the first contacting, the phenolic compound and the hydrogen are in contact with first portion of the hydrogenation catalyst under conditions of a first hydrogenation reaction to obtain first contacted product mixture; and in the second contacting, the first contacted product mixture and supplemental hydrogen are in contact with a second portion of the hydrogenation catalyst under conditions of a second hydrogenation reaction to obtain second contacted product mixture.

3. The method according to claim 2, wherein the first contacting is carried out at a temperature of 60-90° C., and the second contacting is carried out at a temperature of 80-140° C.; and in the first contacting and the second contacting, the pressures are the same or different, and are each 1-5 MPa, the pressures being gauge pressures.

4. The method according to claim 2, wherein the first contacting is carried out in a tubular reactor; and the second contacting is carried out in a fixed bed reactor.

5. The method according to claim 2, wherein a molar ratio of the phenolic compound to the hydrogen to the supplemental hydrogen is 1:4-6:1-4; and the solvent is one or a combination of two or more selected from the group consisting of methanol, ethanol, n-propanol, isopropanol, n-butanol, isobutanol, tert-butanol, methyl acetate, ethyl acetate, n-propyl acetate, isopropyl acetate, n-butyl acetate, sec-butyl acetate, ethylene glycol monomethyl ether, and ethylene glycol dimethyl ether.

6. The method according to claim 1, wherein the phenolic compound shown in Formula I is 2,2-bis(4-hydroxyphenyl) propane and/or bis(4-hydroxyphenyl) methane.

7. The catalyst according to claim 1, wherein the content of the nickel element is 20-60 wt %, the content of the Group VIB metal oxide is 0.1-15 wt %, the content of zirconium oxide is 1-40 wt %, and the content of aluminum oxide is 5-70 wt %, based on the total amount of the catalyst.

8. The method according to claim 1, wherein a molar ratio of the nickel element to zirconium oxide is 2-21:1.

9. The method according to claim 1, wherein the group VIB metal element is molybdenum.

10. The method according to claim 1, the hydrogenation catalyst is prepared by a preparation method comprising the following steps of:

(1) contacting a precipitating agent with a solution comprising a nickel compound and a zirconium compound, and separating a solid phase substance from a mixture resulting from the contacting to obtain a precipitate;

(2) mixing the precipitate with a Group VIB metal compound and an aluminum-containing compound, and drying, calcining and shaping the resulting mixture sequentially to obtain a catalyst precursor, wherein the Group VIB metal compound is Group VIB metal oxide and/or a precursor of Group VIB metal oxide, and the aluminum-containing compound is aluminum oxide and/or a precursor of aluminum oxide; and (3) contacting the catalyst precursor with a reducing agent under conditions of a reduction reaction.

11. The method according to claim 10, wherein in the step (1), the precipitating agent is an inorganic base.

12. The method according to claim 10, wherein in the step (1), the nickel compound is one or two or more selected from the group consisting of nickel sulfate, nickel nitrate, nickel chloride, nickel acetate and nickel formate; and in the step (1), the zirconium compound is one or two or more selected from the group consisting of zirconium sulfate, zirconium nitrate, zirconium oxide and zirconyl nitrate.

13. The method according to claim 10, wherein in the step (1), the contacting is carried out at a pH of 11-12.

14. The method according to claim 10, wherein in the step (2), the Group VIB metal compound is a Group VIB metal oxide; and in the step (2), the aluminum-containing compound is aluminum oxide and/or pseudoboehmite.

15. The method according to claim 10, wherein the nickel compound, the zirconium compound, the Group VIB metal compound and the aluminum-containing compound are used in amounts such that the content of the nickel element is 20-60 wt %, the content of the Group VIB metal oxide is 0.1-15 wt %, the content of zirconium oxide is 1-40 wt %, and the content of aluminum oxide is 5-70 wt %, based on the total amount of the finally prepared catalyst.

16. The method according to claim 10, wherein the Group VIB metal element is molybdenum.

17. The method according to claim 10, wherein in the step (2), the drying is carried out at a temperature of 80-120° C.; and in the step (2), the calcining is carried out at a temperature of 400-600° C.

18. The method according to claim 10, wherein in the step (3), the reducing agent is hydrogen.

* * * * *